United States Patent [19]

Curless et al.

[11] 4,046,137
[45] Sept. 6, 1977

[54] SOLENOID OPERATED BLOOD PUMP DRIVE SYSTEM

[75] Inventors: Richard W. Curless, Nabnasset; Armando Federico, Needham, both of Mass.

[73] Assignee: Avco Corporation, Greenwich, Conn.

[21] Appl. No.: 713,546

[22] Filed: Aug. 11, 1976

[51] Int. Cl.² ........................... A61M 1/03; F04B 9/10
[52] U.S. Cl. .................................. 128/1 D; 417/416; 417/383
[58] Field of Search ................... 128/1 D, 214 R, 273; 3/1.7; 417/383, 389, 390, 416

[56] References Cited
U.S. PATENT DOCUMENTS

| | | | |
|---|---|---|---|
| 3,099,260 | 7/1963 | Birtwell | 128/1 D |
| 3,428,042 | 2/1969 | Chesnut | 128/1 D |
| 3,433,983 | 3/1969 | Keistman et al. | 128/1 D X |
| 3,456,444 | 7/1969 | Rishton | 128/1 D X |
| 3,592,183 | 7/1971 | Watkins et al. | 128/1 D |

*Primary Examiner*—Dalton L. Truluck
*Attorney, Agent, or Firm*—Charles M. Hogan; Melvin E. Frederick

[57] ABSTRACT

A solenoid operated drive system or actuating unit for driving blood pumps such as intra-arterial "balloon" pumps, implantable pulsatile pumps, external pumps and the like, wherein a shaft attached to the movable end of a bellows is caused to move back and forth by a pair of oppositely disposed solenoids. The extent of the excursion of the shaft and hence the movable end of the bellows is variably controlled by a first stopper fixedly attached to the frame and a second stopper fixedly attached to a carriage which is adjustably carried within the frame. The solenoids are alternately actuated and/or controlled by suitable control signals which are keyed to the heartbeat or R wave. At the beginning of each cycle for each solenoid and for a short time thereafter, depending on the cycle, a voltage is applied to provide maximum drive. At the end of the maximum drive portion, a reduced voltage is applied to provide a drive and/or holding force of lesser magnitude and is maintained until after the shaft has stopped moving. Thereafter, the reduced voltage is removed and/or current flow through the solenoid is prevented for a further period of time until the next cycle for this solenoid begins with the application of the high voltage. Adjustable noise reducing bumpers are provided to keep impact noises at a minimum and insure the maintenance of a fixed stopping point over extended periods of time.

15 Claims, 8 Drawing Figures

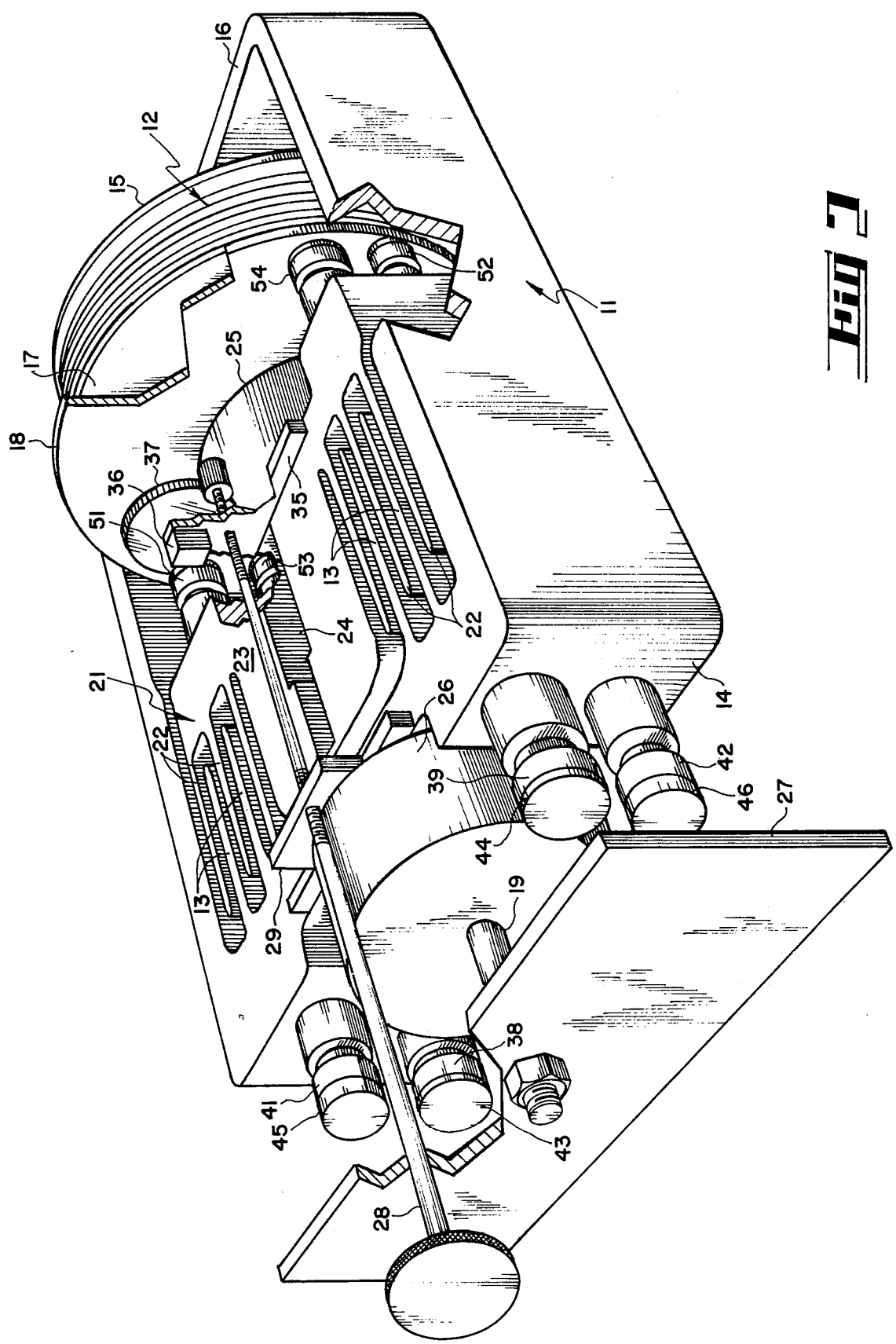

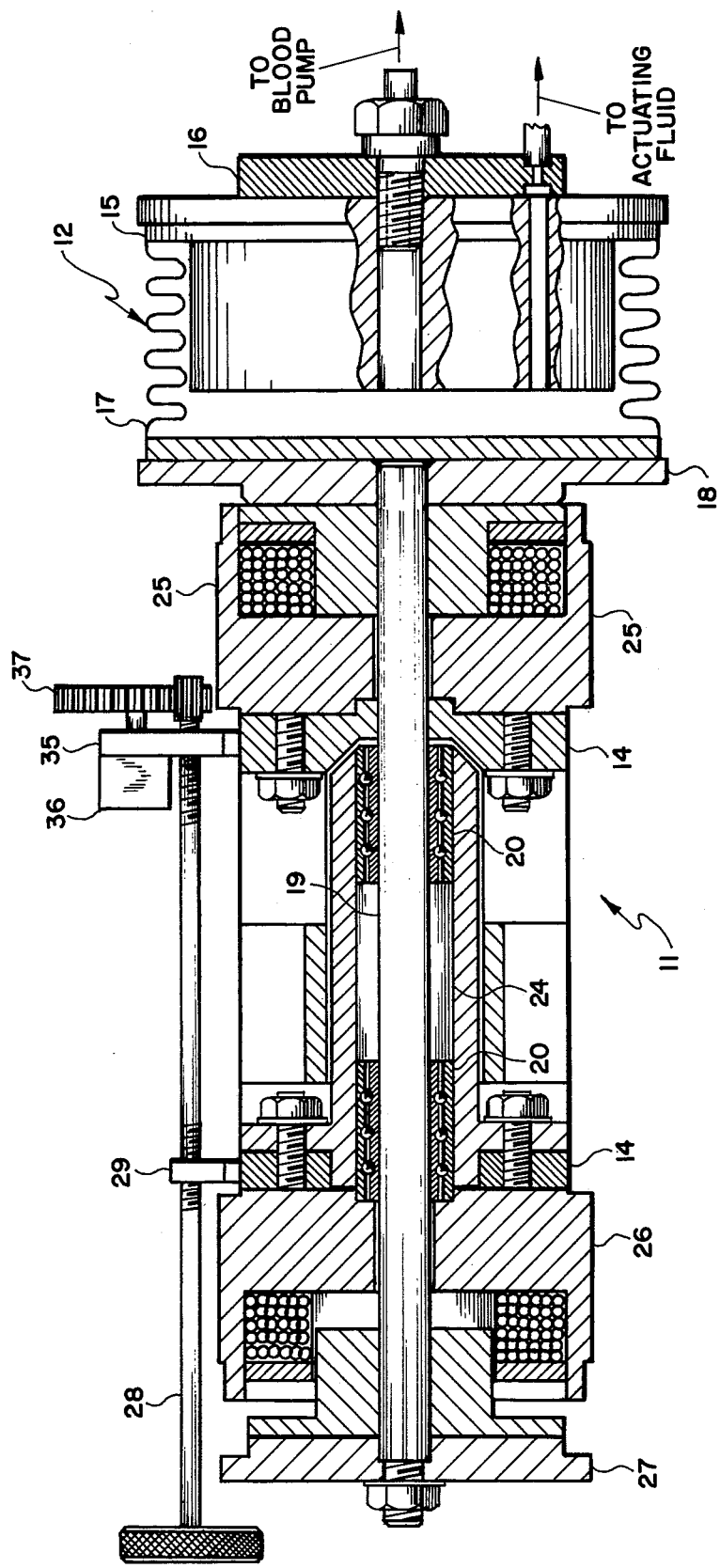

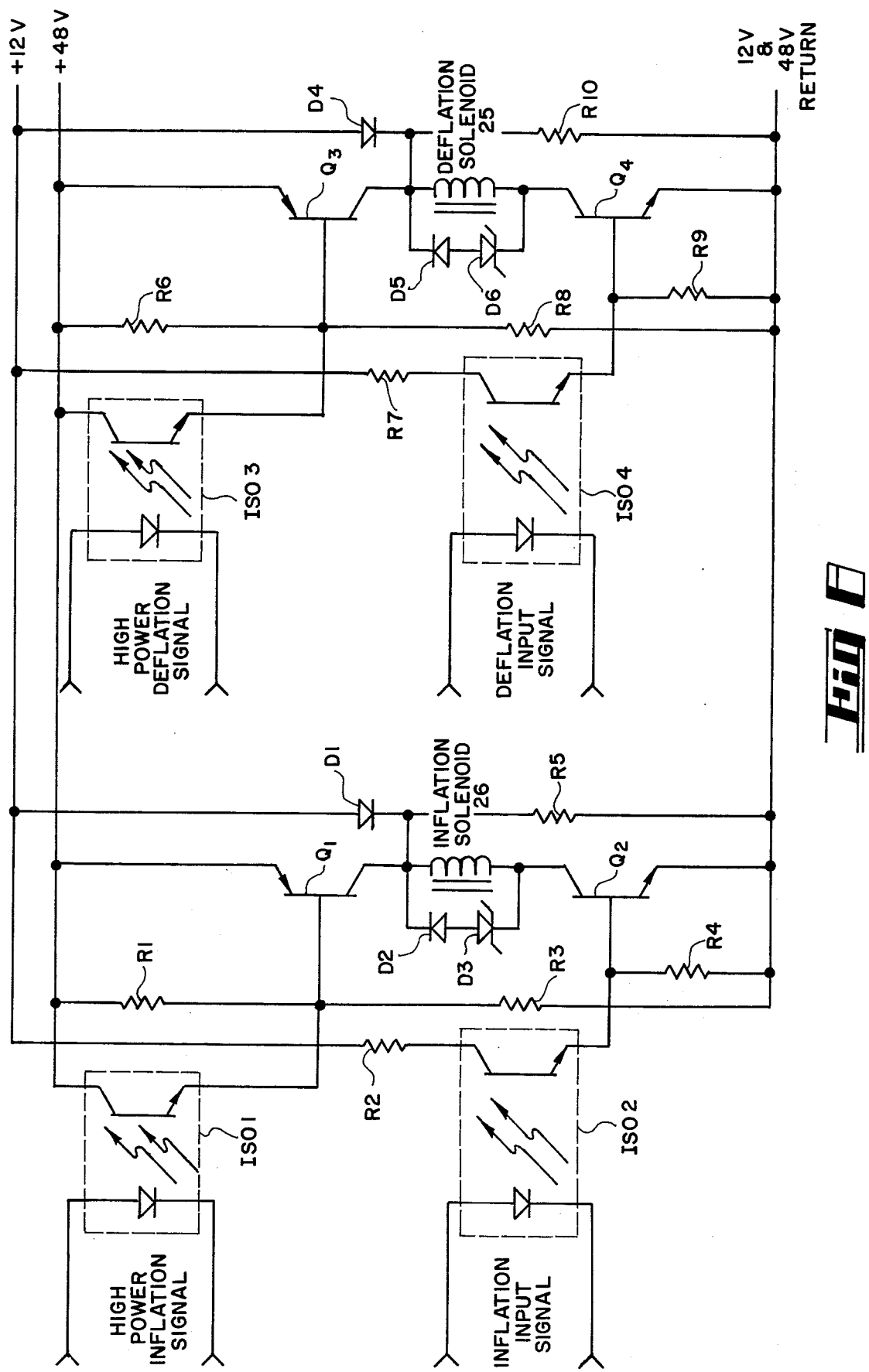

SOLENOID OPERATED BLOOD PUMP DRIVE SYSTEM

BACKGROUND OF THE INVENTION

This invention relates to circulatory assist systems and more particularly to actuating units for driving blood pumps in circulatory assist systems.

The advent of open heart surgery has presented to the medical profession the opportunity of repairing damaged or diseased hearts of individuals and where appropriate, using circulatory assist systems in individuals who, without such correction and/or systems, face premature death. Many devices are involved in this type of surgery. For example, one type of circulatory assist system comprises an auxiliary ventrical or valveless blood pump connected across the arch of the aorta and is driven by fluid pressure in response to electronic signals (QRS wave) provided by the heart itself. By operating the blood pump or auxiliary ventricle in proper phase, the systolic pressure in the left heart can be reduced and the systemic circulation can be maintained with a substantially reduced work load on the heart muscle. In addition, the operation of the auxiliary ventricle has the effect of shifting the phase of the normal systolic pressure so that this pressure appears in the aorta at a time when the left ventricle is relaxed. Assuming competence of the normal aortic valve, one then has an increased perfusion pressure available to the coronary arteries. It is believed that such an increase in coronary perfusion, together with a reduction in the effort required from the heart, should be effective in a number of cases of cardiac insufficiency.

Another circulatory assist system presently used to some considerable extent is one utilizing intro-arterial balloon pumping. In this technique an inflatable intra-arterial device or "balloon" on a catheter is typically inserted through a femoral artery and passed up the arterial tree into the decending aorta. When in place in the aorta, the balloon is sequentially inflated and deflated to provide the necessary circulatory assistance. For a description of such a balloon and typical prior art systems associated therewith, reference is made to U.S. Pat. Nos. 3,452,738, issued July 1, 1969, 3,456,444, issued July 22, 1969, and 3,504,662, issued Apr. 7, 1970, which are incorporated herein as if set out at length.

Other techniques are known and include left-heart bypass and diastolic augmentation.

As may be seen from the above, one important component of circulatory assist systems is a pump that either assumes the heart's role of pumping blood or which reduces the work load of the heart muscle. By using heart pump equipment for extended periods of time, it is contemplated that the equipment may be utilized for regional perfusions in therapeutic treatment of the heart. Still another use of such equipment is to provide circulation of blood through an artificial organ such as an external artificial kidney. In connection with this function of the apparatus, it should be noted that many research institutions at this time are concentrating their research activities on providing artificial counterparts of other organs, and whenever such application requires circulation, the present invention may be utilized.

In the use of circulatory assist systems, it is desirable if not necessary to be able to control the blood pump through an actuating unit that is pneumatically operated to eject an operating fluid to drive the blood pump in a manner to meet the requirements of a patient's circulatory system. The actuating unit embodied in the present invention satisfies all of the requirements for an actuating unit set forth above and has been proved successful in carrying out the difficult task of driving a blood pump under various types of conditions.

Accordingly, it is an object of the present invention to provide an actuating unit for driving a blood pump.

Another object of the present invention is to provide an actuating unit that is simple in construction and operation and that is not susceptible to breakdown.

A further object of the present invention is to provide an automatically operated actuating unit for operating a heart pump wherein the actuator is adapted to control a hydraulic pulse for actuating a pump unit or ventricle to move an equal volume of blood through or past the blood pumping unit.

A still further object of the invention is to provide an actuating unit in a circulatory assist system that is simple in construction, quiet in operation, requires a minimum amount of power to operate and that will accurately and consistently provide selectable different volumetric displacements for driving different size blood pumps.

The novel features that are considered characteristic of the present invention are set forth in the appended claims, the invention are set forth in the appended claims, the invention itself, however, both as to its organization and method of operation, together with additional objects and advantages thereof, will best be understood from the description of a specific embodiment when read in conjunction with the accompanying drawings, in which:

FIG. 2 is a perspective view with parts borken away of an actuating unit in accordance with the invention;

FIG. 3 is a sectional side view of the actuating unit shown in FIG. 2;

FIG. 8 is a schematic diagram of means for controlling the voltages supplied to the solenoids.

DESCRIPTION OF AN EMBODIMENT OF THE INVENTION

Figure 1:
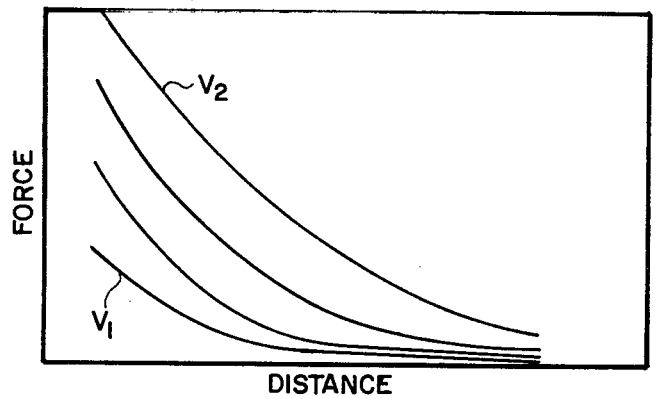
FIG. 1 is a graphic illustration of the force exerted by a solenoid, versus displacement for different applied voltages.

Directing attention now to FIG. 1 which illustrates the force exerted by a solenoid versus displacement of a member for different applied solenoid voltages, it may be seen that for motion of the member toward the solenoid (right to left in FIG. 1), the force acting on the member by the solenoid increases as the member gets closer to the solenoid. It may also be seen that as the solenoid voltage is increased for any given location the force on the member increases. Further we have found that while a large solenoid voltage is desirable to initiate movement, upon the member reaching a stopping point, the force exerted by this voltage is generally much higher than desired or necessary. Accordingly, in accordance with one feature of the invention, for each cycle a first voltage is provided to the appropriate solenoid to initiate and support movement and then the voltage is reduced to both provide a desired lower impact force and hold the member at its stopping point, all with a minimum expenditure of power and minimum impact noise.

Directing attention now to FIGS. 2 and 3, there is shown apparatus in accordance with the invention comprising a generally heavy metal rectangular frame member 11 having a bellows 12 disposed at one end within it. Narrow, elongated fins 13 spaced one from another are provided, integral with the opposite end portion 14 of the frame and extending toward but stopping some distance short of the bellows 12. The remote end 15 of the bellows 12 is fixedly attached to the end portion 16 of the frame member 11, the other end 17 of the bellows 12 being provided with a metal plate 18 which together with this end 17 of the bellows is movable toward and away from the fixed end 15 of the bellows.

A central shaft 19 is axially attached to the bellows plate 18 and via a suitable bearing, sleeve, or the like 20 in carriage member 21, extends through and past carriage member 21 and the opposite end portion 14 of the frame member 11. Disposed within the frame member 11 intermediate plate 18 and the frame fins 13 is relatively heavy metal carriage member 21 having fins 22 that are interposed and extend between the frame fins 13, such that the carriage member 21 may move within the frame member 11 toward and away from the bellows plate 18. The center porton 23 of the carriage member 21 is provided with a passage or open portion 24 and bearings 20 to receive shaft 19 and a deflation cycle solenoid 25 is carried on the front portion of the carriage member 21, the shaft 19 passing through the center thereof for connection with plate 18. Similarly, and inflation cycle solenoid 26 is carried on the rear end portion 14 of the frame member 11 with the shaft 19 also passing through its center. A metal rear plate 27 is attached to the end of the shaft 19, whereby it may be attracted toward the inflation solenoid 26 when this solenoid is coupled to a source of current.

An adjustable shaft 28 rotatably carried by a right-hand threaded projection 29 of the end portion 14 of the frame member 11 extends through a projection 35 at the front portion of the carriage member 21 and is provided with left-hand threads at this point which engage mating threads in the projection 35. A potentiometer 36 carried by the projection 35 is driven via gears 37 by shaft 28 to provide an output signal indicative of the position of the carriage member 21 within the frame member 11. Thus, when the adjusting shaft 28 is rotated, the carriage member 21 is caused to be moved within the frame member 11, thereby providing means for selectably adjusting the position of the carriage member within the frame member for the purpose of varying the length of the stroke of shaft 19 and hence, the volumetric displacement of te bellows 12.

Since the bellows plate 17 is axially disposed adjacent the deflation solenoid 25 carried by the movable carriage member 21, and the end plate 27 is axially disposed adjacent the inflation solenoid 26 carried by the frame member 11, it will now be apparent that upon application of the proper voltage to the deflation solenoid 25, the bellows 12 will be extended in length and that the end plate 27 will move away from the infaltion solenoid 26. Similarly, it will now also be seen that when the proper voltage is applied across the inflation solenoid 26, the reverse of the above will occur and the bellows 12 will be compressed or reduced in length.

For purposes of stopping motion of shaft 19, its associated plates 18 and 27 and the bellows 12, with a minimum of noise and tendency to rebound, two sets of two adjustable bumpers 38–39 and 41–42 are carried by end portion 14 of the frame to engage end plate 27. The extreme exposed end surfaces of the first set of bumpers 38–39 are each provided with a relatively thin piece of compressible material 43–44, while the extreme exposed end surfaces of the second set of bumpers 41–42 are each provided with a thicker piece of identical compressible material 45–46. The second set of bumpers 41–42 are adjusted so that they first engage the end plate 27 and are partially compressed before the end plate engages the second set of bumpers 38–39.

The above-described arrangement of bumpers has been found to result in minimum inpact noise level and to provide substantially constant deceleration of the end plate 27. Further, while adjustable toward and away from the frame 11, they also provide a substantially constant fixed stopping point for plate 27 over extended periods of use. The use of different thicknesses of the compressible material is believed to be effective in the reduction of creep of the compressible material over extended periods of use. A suitable compressible material is E-A-R energy absorbing material, manufactured and sold by National Research Corporation, Billerica, Massachusetts. Bumpers 38–39 are diagonally loated with respect to each other as are also bumpers 41–42 as shown in FIG. 1 to keep distortation of end plate 27 at a minimum.

Adjustably disposed and arranged on the front surface of the carriage member 21 are two sets of bumpers 51–52 and 52–54 substantially identical to those previously described and which operate in substantially the same manner to provide the same result. The two sets of bumpers on the carriage member 21 engage the bellows plate 18. Preferably, the frame and carriage are both of substantial mass to facilitate the removal of heat generated by the solenoids during use and to provide the necessary strength for accurate alignment and to prevent distortation during use.Further, a blower fan, or the like, (not shown) may be provided above one surface of the carriage member and arranged and adapted to direct a constant stream of air past the fins of the frame and carriage members to remove heat therefrom. The fins provide a large surface area for more efficient heat removal which might otherwise cause excessive heating of the solenoids, frame and/or carriage member.

When used for driving intra-aortic balloons, the bellows, solenoids and associated components should be selected to accommodate the maximum anticipated loading, such as, for example, to deliver 40 cc at a back pressure of up to 150 mm. In such cases, a typical load may be 40 cc at 75–100 mm back pressure. Of course, if used in connection with children and/or small adult patients, the bellows may need only provide about 20 cc displacement at a back pressure of, perhaps, less than 75–100 mm. depending on the physical condition and stature of the patient.

Helium has been found to be a satisfactory gas to use to charge the bellows and tubing coupling the bellows and the blood pump being used. The desired fill pressure is provided by charging the bellows (and coupled blood pumping unit) from a suitable source of actuating fluid to the desired pressure.

As previously pointed out, the present invention, while not so limited, is particularly useful for driving intra-aortic balloons for heart assist. Such ballons come in various sizes—typically 20, 30 and 40 cc—so as to accommodate various sized patients. The drive pump or actuating unit for causing inflation and deflation of the balloons must accordingly not only have the capability that it can be adjusted readily to pump at different rates to respond to different and variable heart beat rates of patients, but also to provide the necessary different volumetric outputs at different back pressures. A third requirement is that the drive pump be quiet, and a fourth requirement is that the volumetric output, once set, must remain essentially constant at the set value during, at least, the period of operation (days) which may consist of tens of thousands of cycles. Lastly, the drive pump must possess a high degree of relitability.

In one present day widely used technique, the method of inflating and deflating the balloon comprises alternately connecting one side of a chamber divided by a diaphragm first to a pressure source and then a vacuum source. This causes the diaphragm to move alternately such as to pressurize or rarefy a suitable gas, such as helium on the balloon side of the diaphragm which is connected through a catheter to the balloon. The alternate pressurization and rarefication of the helium inflates and deflates the balloon against the back pressure of the patient's system. The volume pumped is selectably varied by means of an adjusting screw which limits the excursion of the diaphragm.

As may now be readily seen, a pump in accordance with the present invention includes a bellows attached to a shaft which is driven alternately back and forth by two solenoids. The excursion of the shaft is determined in part by two sets of four bumpers, one set being attached to the frame, the other set being attached to the movable carriage. Two solenoids are utilized to attract or pull rather than push. Thus, the shaft moves first in one direction and then the other, causing the bellows to alternately contract and expand, compressing or rarefying the driving gas it contains. The driving gas from the bellows, in conventional manner, flows through a catheter and into or out of a balloon, or the like, causing actuation thereof as by expansion or contraction. The necessary amount of gas forced into a balloon by the action of the bellows, other factors being constant, is determined by the distance that the shaft attached to the bellows moves. This distance and therefore the volume pumped, is determined by the separation between two sets of stoppers or bumpers. Accordingly, the separation, and thus the volume pumped, may be varied by turning the threaded shaft which causes the carriage on which one of te solenoids and one set of bumpers is mounted to move with respect to the other solenoid and other set of bumpers. The extent of the separation is sensed by potentiometer 36 driven by the threaded shaft 28. The resistance of potentiometer 36 is a function of the number of turns of the threaded shaft and is calibrated in terms of balloon volume which may be displayed automatically. Because the drive pump must be quiet and because the volume to be pumped, once set, must remain fixed, the end surfaces of the bumpers are provided with a material which absorbs the mechanical energy, results in minimum impact noise and which is provided in a manner to reduce creep.

Directing attention now to the mode of operation of the drive pump of FIG. 2 and FIG. 3, it has previously been noted that for each cycle of inflation and then deflation, a first acutating voltage is applied to the appropriate solenoid and after a predetermined delay, the voltage across the solenoid is reduced to a lower value.

Figure 4:
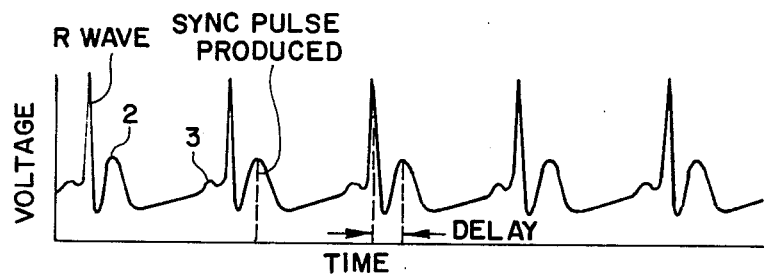
FIGS. 4–7 show a typical relationship between trigger pulses derived from the R wave, the voltages on the solenoids for the compression and deflation strokes, and the pressure in the bellows during compression and deflation.
Figure 5:
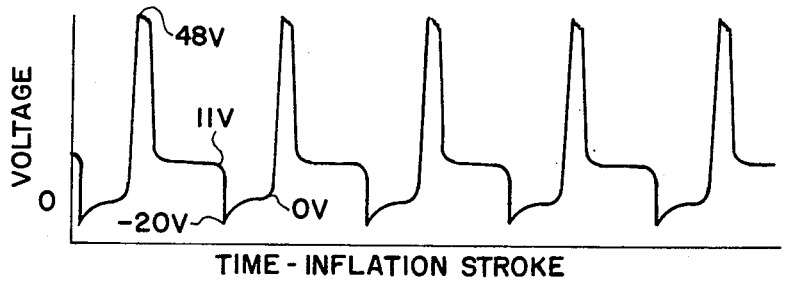
Figure 6:
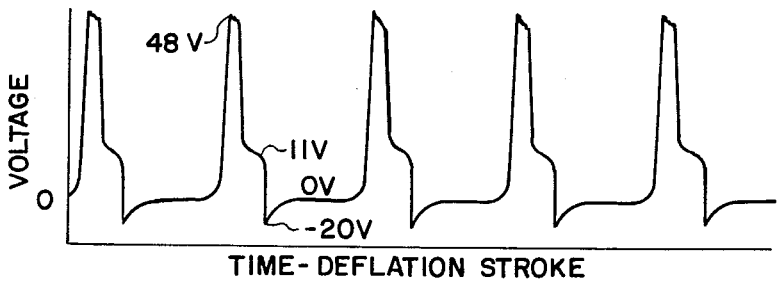

FIGS. 4–7 illustrate the relationship of the solenoid voltages and bellows pressure to a patient's R wave timing pulse derived in conventional manner. Thus, in FIG. 4, the numerals 2 and 3 designate respectively the beginning and end of the systolic pulse of the heart. Also shown is the R wave from which conventional timing pulses are derived in conventional manner. For this purpose, the output of an EKG unit as shown in FIG. 4 may be fed into an amplifier and synchronizer pulse circuit (not shown) this is adapted to recognize the R wave and delay it a percentage of the R to R interval and use it for synchronizing functions with the patient's heart. Since the hydraulic events in the patient's heart are not simultaneous with the ECG unit or the R wave, it is desirable to provide means for phasing the timing pulse of the drive unit with the heat in order to accommodate these time delays and provide any desired time delay. For this purpose, a conventional network (not shown) triggered by the R wave as shown in FIG. 4 may be provided to create a sync pulse delayed behind the R wave by a controlled amount to enable the pulse fo the drive unit to be delayed beyond the systolic interval of the patient's heart by an appropriate time interval. By providing this time delay interval (see FIG. 4), the drive unit may be adjusted so that the drive unit will be properly phased with the patient's diastolic interval in such a way as to physiologically aid the patient's heart.

The sync pulse produced by the aforementioned delay network may be utilized to actuate a trigger circuit which may include a control circuit which is provided for controlling the duration of the trigger circuit. For a further discussion of suitable synchronizing circuits for different applications, reference is made to the aforementioned U.S. Pat. No. 3,099,260.

Returning now to FIGS. 4–7, and assuming a constant time delay interval between R wave sync pulses, (which, incidentally, is not always the case), it may be seen from FIGS. 4–6 that at the appropriate time, a sync pulse causes a maximum voltage of, for example, about 48 volts, to be applied to the inflation solenoid 26 and maintained for some predetermined and adjustable portion of the total period between sync pulses. The maximum voltage is applied only for that portion of the total period sufficient to bring the end plate 27 into close proximity with the inflation solenoid 26 where the force exerted by it on end plate 27 is high. At this point, the voltage across the inflation solenoid 26 is reduced to a lower value, such as, for example, 11 volts sufficient to insure continued movement of end plate 27 and to hold end plate 27 at its stopping point determined by the bumpers. Preferably, end plate 27 is held in its stopped position by the low voltage for a time sufficient to permit the pressure of the gas in the bellows and the balloon to become equalized and thereby assure inflation of the blloon to the same size during each inflation cycle.

After completion of the inflation cycle, the lower holding voltage on the inflation solenoid 26 is removed and the positive high voltage is applied to the deflation solenoid 25. However, because the pressure on the balloon pump tends to aid in the reversal of the motion of the bellows, in this case, the high voltage need only be applied for a time less than that required for the desired inflation stroke rate. When the bellows plate 18 is sufficiently close to the deflation solenoid 25, the high voltage is reduced to the low voltage level and held to the end of the delfation cycle, whereafter the inflation cycle, as described above, is repeated.

Figure 7:
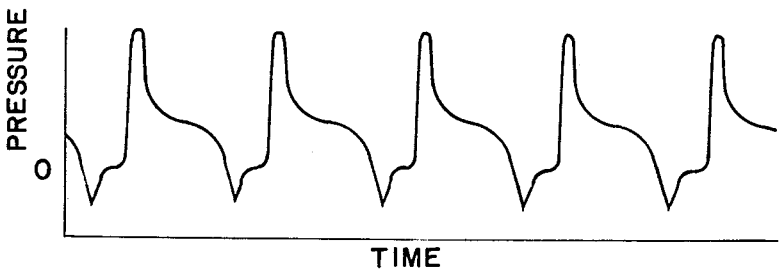

FIG. 7 illustrates the variation in pressure in the bellows 12 during the inflation and deflation cycles.

To accommodate variations in pulse rates and/or regularity, means (not shown) are advantageously provided for varying the beginning and ending times of the voltages applied to the solenoids.

Attention is now directed to FIG. 8 which shows means for controlling the actuation of the solenoids 25 and 26.

Beginning with the inflation cycle, an inflation input drive pulse derived from the R wave at the desired and selectable time is applied to an optical isolator IS02 which causes its receiver portion to turn on and permit current to flow to the base of transistor Q2 through bias resistor R2. At the same time, in coincidence with the provision of the inflate drive pulse, a high power inflate pulse is applied to optical isolator IS01 causing its previously closed receiver portion to open and prevent the flow of current therethrough. When these two actions occur, the flow of current through bias resistor R3 results in the forward bias of transistor Q1 and current flow from its base, thereby causing transistor Q1 to begin conducting. Transistors Q1 and Q2 are driven to the saturated state and when this occurs, the collector of transistor Q1 rises very close to the high voltage level of, for example, 48 volts. With this high voltage on the collector of transistor Q1, diode D1 is reversed biased and this prevents the flow of current from the low voltage supply such as, for example, 12 volts.

For the arrangement shown in FIG. 8 and described above, as long as the high power inflate pulse is supplied to the optical isolator IS01, transistor Q1 will conduct and maximum power is supplied to the inflation solenoid 26.

As previously pointed out, this causes the bellows 14 to move in the direction to cause drive gas to be forced into a balloon or the like. A short and selectable time (of the order of 50 to 125 ms) after beginning the inflate cycle, the high power inflate pulse is removed. When this occurs, transistor Q1 is forced into the off or non-conducting state and current flow from the high voltage source to the inflate solenoid 26 is blocked.

When transistor Q1 ceases conducting its collector voltage drops, and when this voltage drops below the low voltage supply, diode D1 becomes forward biased and begins to conduct. When diode D1 begins to conduct, only the low voltage supply supplies current to the inflate solenoid 26. The operation of inflate solenoid 26 at its low level prevails as long as the inflation input drive signal is applied to optical isolator IS01. Accordingly, where a balloon is being driven, the balloon will remain in the inflated state so long as the inflation input drive is applied to optical isolator IS02. The delfation cycle is begun by removing the inflation input dirve signal which, in turn, causes transistor Q2 to cease conducting and block current flow to the inflate solenoid 26.

Upon transistor Q2 ceasing conducting, conduction through diodes D2 and D3 aid in the removal of the back field of the inflate solenoid 26.

Simultaneously with the removal of the inflation drive input signal, a deflation drive input signal is applied to optical isolator IS04 and a high power deflation signal is applied to optical isolator IS03.

The operation for the deflation cycle of optical isolators IS03 and IS04, together with transistors Q3 and Q4, is substantially the same as that of optical isolators IS01, IS02 and transistors Q1 and Q2 for the inflation pulse. Thus, with an actuating signal suplied to optical isolator IS03, its receiver portion is turned off and current flow is blocked. When this happens, bias resistor R6 forward bias transistor Q3. Optical isolator IS04 is turned on by the deflation input signal and conducts current through resisotr R7 to the base of transistor Q4. Inasmuch as both bases of transistors Q3 and Q4 are now conducting current, both of these transistors are saturated and permit current flow from the high voltage supply to flow through the deflation solenoid 25. Actuation of the deflation solenoid 25 results in elongation of the bellows and the deflation cycle. Again, as previously noted, the duration of the high power deflate cycle is less than that of the high power inflation cycle and may be selectably variable up to about 125 ms.

The low power deflate cycle is initiated by removal of the high power input signal which causes transistor Q3 to cease conduction and remove the deflate solenoid from the high voltage supply. As the voltage on the collector of transistor Q3 drops, diode D4 is forward biased when this voltage drops below that of the low voltage supply. Conduction of diode D4 connects the deflate solenoid 25 to the low voltage supply and this condition remains until the deflation input signal is removed. The deflation input signal is removed at the beginning of a new inflation cycle and the inflation cycle is repeated.

The various features and advantages of the invention are thought to be clear from the foregoing description. Various other features and advantages not specifically enumerated will undoubtedly occur to those versed in the art, as likewise will many variations and modifications of the preferred embodiment illustrated, all of which may be achieved without departing from the spirit and scope of the invention as defined by the following claims:

1. In a system for assisting and/or providing blood flow in a living body comprising a blood pumping unit, a source of actuating fluid, and means for providing a synchronizing trigger signal for synchronizing the operation of said blood pumping unit with the pumping action of the heart, an actuating unit for periodically supply operating fluid to actuate said blood pumping unit to produce an augmented stroke in synchronism with the diastolic period of the pumping action of the heart comprising:
   a. a rigid frame member having an opening therein;
   b. a carriage member movably disposed within said frame member opening;
   c. a first solenoid carried by said frame member;
   d. a second solenoid carried by said carriage member and oppositely disposed to said first solenoid;
   e. bellows means carried by said frame member, said bellows means being adapted for connection to said source of actuating fluid and to supply actuating fluid to said blood pumping unit;
   f. first and second movable plate members rigidly interconnected and operatively associated with said solenoids and bellows means whereby when current is sequentially supplied to said solenoids, said plates are magnetically attracted by said solenoids and said bellows mens ae actuated to vary the volumetric content thereof; and
   g. means adapted to be actuated by said trigger signal for applying a series of two voltages comprising a first voltage and then a second lower voltage alternately to said first and second solenoids, said second voltage in each case being applied upon termination of said first voltage whereby upon actuation by said trigger signal, said augmented stroke is produced in synchronism with the diastolic period of the pumping action of the heart.

2. The combination as defined in claim 1 and additionally including stopping means for separately stopping said first and second plate members as predetermined points when they are traveling toward their respective solenoids.

3. The combination as defined in claim 2 and additionally including:
   a. adjusting means for varying the position of said carriage member in said frame member; and
   b. means actuated by said adjusting means to provide an indication indicative of the position of said carriage member, said indiction being calibrated in terms of the maximum pumping volume of said blood pumping unit.

4. The combination as defined in claim 3 wherein said solenoids, plate members and bellows means are all located on a common axis and said bellows means are sequentially elongated and compressed when said plate members are attracted by said solenoids.

5. The combination as defined in claim 2 wherein said first voltage is terminated and said second voltage applied before said plate members contact said stopping means.

6. The combination as defined in claim 5 wherein said first voltage has a magnitude sufficient to cause said plate members to begin movement from rest, and said second voltage has a magnitude sufficient to cause said plate members to continue moving after termination of said first voltage.

7. The combination as defined in claim 6 wherein said second voltage is applied to each of said solenoids until after the plate member associated with each of said solenoids contacts its respective stopping means.

8. In a system for assisting and/or providing blood flow in a living body compriing a blood pumping unit, a source of actuating fluid, and means for providing a synchronizing trigger signal for synchronizing the operation of said blood pumping unit with the pumping action of the heart, an actuating unit for periodically supplying operating fluid to actuate said blood pumping unit to produce an augmented stroke in synchronism with the diastolic period of the pumping action of the heart comprising:
   a. a substantially rigid frame member having oppositely disposed first and second end portions and an opening intermediate said first and second end portions;
   b. bellows means having a first end fixedly carried by said frame member first end portion and a second end movable toward and away from said first end to vary the volumetric content of said bellows means, said second end having a first exposed metal plate member fixedly carried thereby and said bellows means being adapted for connection to said source of actuating fluid and to supply actuating fluid to said blood pumping unit;
   c. carriage member means movably disposed in said frame member oening, said carriage member means having an electrically actuated first solenoid fixedly attached thereto and disposed adjacent the facing said bellows means first metal plate member whereby said first plate member is attracted by said first solenoid when current is supplied to said first solenoid;
   d. a second electrically actuated solenoid fixedly carried by and exterior of said frame member second end portion;
   e. a second metal plate disposed adjacent and facing said second solenoid and exterior of said frame member whereby said second plate is attracted by said second solenoid when current is supplied to said second solenoid;
   f. means for rigidly interconnecting said first and second plates;
   g. means for selectably varying the position of said carriage member means between said first and second plate members; and
   h. means adapted to be actuated by said trigger signal for applying a series of two voltages comprising a first voltage and then a second lower voltage alternately to said first and second solenoids, said second voltage in each case being applied upon termination of said first voltage whereby upon actuation by said trigger signal, said augmented stroke is produced in synchronism with the diastolic period of the pumping action of the heart.

9. The combination as defined in claim 8 and additionally including stopping means for separately stopping said first and second plate members at predetermined points when they are traveling toward their respective solenoids.

10. The combination as defined in claim 9 and additionally including:
    a. adjusting means for varying the position of said carriage member in said frame member; and
    b. means actuated by said adjusting means to provide an indication indicative of the position of said carriage member, said indication being calibrated in terms of the maximum pumping volume of said blood pumping unit.

11. The combination as defined in claim 10 wherein said solenoids, plate members and bellows means are all located on a common axis and said bellows means are sequentially elongated and compressed when said plate members are attracted by said solenoids.

12. The combination as defined in claim 9 wherein said first voltage is terminated and said second voltage applied before said plate members contact said stopping means.

13. The combination as defined in claim 12 wherein said first voltage has a magnitude sufficient to cause said plate members to begin movement from rest, and said second voltage has a magnitude sufficient to cause said plate members to continue moving after termination of said first voltage.

14. The combination as defined in claim 13 wherein said second voltage is applied to each of said solenoids until after the plate member associated with each of said solenoids contacts its respective stopping means.

15. The combination as defined in claim 14 wherein said stopping means comprises:
    a. a first set of four projections carried by and exterior of said frame member second end portion and facing said second plate member; and
    b. a second set of four projections carried by said carriage member means and facing said first metal plate member, each of said first and second sets of projections having compressible and shock absorbing material disposed on their exposed end surfaces adapted to engage said plate members, the compressible material on two projections of each said set being thicker than the compressible material on the remaining two projections, said two projections contacting said plate members before said remaining two projections.

* * * * *

UNITED STATES PATENT AND TRADEMARK OFFICE
CERTIFICATE OF CORRECTION

PATENT NO. : 4,046,137

DATED : September 6, 1977

INVENTOR(S) : Richard W. Curless and Armando Federico

It is certified that error appears in the above-identified patent and that said Letters Patent are hereby corrected as shown below:

Column 2, line 36, for "borken" read --broken--; Column 3, line 26, for "porton" read --portion--; Column 3, line 53, for "te" read --the--; Column 3, line 61, for "infaltion" read --inflation--; Column 4, line 13, for "inpact" read --impact--; Column 4, line 24, for "loated" read --located--; Column 4, line 30, for "52-54 read --53-54--; Column 5, line 12, for relitability" read --reliability--; Column 5, line 48, for "te" read --the--; Column 6, line 5, for "conventinal" read --conventional--; Column 6, line 8, for "this" read --that--; Column 6, line 14, for "heat" read --heart--; Column 6, line 20, for "fo" read --of--; Column 6, line 54, for "blloon" read --balloon--; Column 6, line 65, for "delfation" read --deflation--; Column 7, line 48, for "IS01" read --IS02--; Column 7, line 51, for "delfation" read --deflation--; Column 7, line 52, for "dirve" read --drive--; Column 8, line 4, for "resisotr" read --resistor--; Column 8, line 41, for "supply" read --supplying--; Column 8, line 60, for "mens ae" read --means are--; Column 9, line 5, for "as" read --at--; Column 9, line 14, for "indiction" read --indication--; Column 9, line 37, for "compriing" read --comprising--; Column 9, line 60, for "oening" read --opening--; and Column 9, line 62, for "the" read --and--.

Signed and Sealed this

Twentieth Day of December 1977

[SEAL]

Attest:

RUTH C. MASON
*Attesting Officer*

LUTRELLE F. PARKER
*Acting Commissioner of Patents and Trademarks*